United States Patent
Shanker et al.

(10) Patent No.: US 11,098,005 B2
(45) Date of Patent: Aug. 24, 2021

(54) METHODS FOR PRODUCING (6S,15S)-3,8,13,18-TETRAAZAICOSANE-6, 15-DIOL

(71) Applicant: Panbela Therapeutics, Inc., Waconia, MN (US)

(72) Inventors: P. Sathya Shanker, Bangalore (IN); Sankappa Rai U, Bangalore (IN); Murali Venghatraghavan, Hosur (IN); Selvam Vengatesan, Uthungari (IN); Rahul Patil, Bangalore (IN); Padavalachandu Bharathkumar, Bangalore (IN)

(73) Assignee: Panbela Therapeutics, Inc., Waconia, MN (US)

( * ) Notice: Subject to any disclaimer, the term of this patent is extended or adjusted under 35 U.S.C. 154(b) by 0 days.

(21) Appl. No.: 16/939,500

(22) Filed: Jul. 27, 2020

(65) Prior Publication Data
US 2021/0009504 A1    Jan. 14, 2021

Related U.S. Application Data

(63) Continuation of application No. PCT/US2019/015581, filed on Jan. 29, 2019.

(60) Provisional application No. 62/623,641, filed on Jan. 30, 2018.

(51) Int. Cl.
C07C 213/02 (2006.01)
C07C 215/18 (2006.01)

(52) U.S. Cl.
CPC .......... *C07C 213/02* (2013.01); *C07C 215/18* (2013.01)

(58) Field of Classification Search
None
See application file for complete search history.

(56) References Cited

U.S. PATENT DOCUMENTS

| | | | |
|---|---|---|---|
| 5,962,533 | A | 10/1999 | Bergeron, Jr. |
| 6,160,022 | A | 12/2000 | Bergeron, Jr. |
| 9,303,001 | B2 | 4/2016 | Zhang et al. |
| 2008/0108706 | A1 | 5/2008 | Bergeron et al. |
| 2013/0137772 | A1 | 5/2013 | Bergeron et al. |

FOREIGN PATENT DOCUMENTS

WO    2017062704 A1    4/2017

OTHER PUBLICATIONS

Bergeron, Raymond J. et al., "Synthesis and Evaluation of Hydroxylated Polyamine Analogues as Antiproliferatives", J. Med. Chem. 2000. vol. 43, 2000, 224-235.
International Search Report for International Application No. PCT/US19/15581 dated Apr. 15, 2019.

*Primary Examiner* — Sudhakar Katakam
*Assistant Examiner* — Jennifer C Sawyer
(74) *Attorney, Agent, or Firm* — Elmore Patent Law Group, P.C.; Edgar W. Harlan; Carolyn S. Elmore

(57) ABSTRACT

The present invention provides methods of synthesizing (6S,15S)-3,8,13,18-tetraazaicosane-6,15-diol and salts thereof.

17 Claims, No Drawings

METHODS FOR PRODUCING (6S,15S)-3,8,13,18-TETRAAZAICOSANE-6, 15-DIOL

RELATED APPLICATIONS

This application is a continuation of International Application No. PCT/US2019/015581, which designated the United States and was filed on Jan. 29, 2019, published in English, which claims the benefit of U.S. Provisional Application No. 62/623,641, filed on Jan. 30, 2018. The entire teachings of the above applications are incorporated herein by reference.

BACKGROUND OF THE INVENTION

The compound (6S,15S)-3,8,13,18-tetraazaicosane-6,15-diol is shown below,

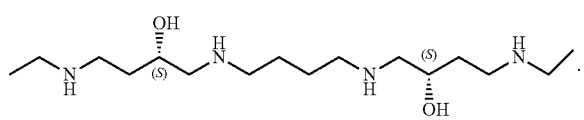

This compound is of use in the resection of the exocrine pancreas and in the treatment of pancreatitis and other diseases and disorders of the pancreas (see, for example, U.S. Pat. No. 6,160,022 and WO 2017/062704).

SUMMARY OF THE INVENTION

The present invention provides methods of synthesizing (6S,15S)-3,8,13,18-teraazaicosane-6,15-diol which are simpler and more efficient than previously disclosed methods.

In one embodiment, the invention relates to a method of producing (6S,15S)-3,8,13,18-teraazaicosane-6,15-diol (Compound 1), comprising the steps of:

(a) reacting a compound of Formula (I),

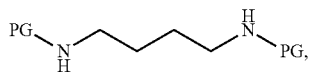

wherein each PG is an amino protecting group,
with a compound of Formula (II),

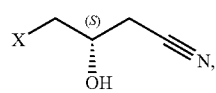

wherein X is a leaving group,
thereby producing a compound of Formula (III),

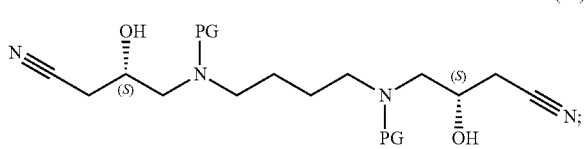

(b) reacting the compound of Formula (III) with a reducing agent, thereby producing a compound of Formula (IV),

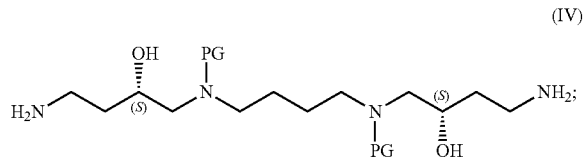

(c) reacting the compound of Formula (IV) with an acetylating agent thereby producing a compound of Formula (V),

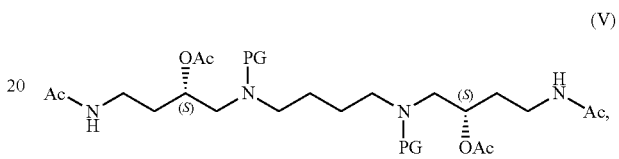

(d) reacting the compound of Formula (V) with a reducing agent, thereby producing a compound of Formula (VI),

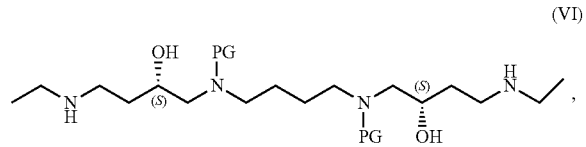

and (e) deprotecting the compound of Formula (VI), optionally in the presence of an acid, thereby producing Compound 1 or a salt thereof.

DETAILED DESCRIPTION OF THE INVENTION

The present invention provides an improved method for producing Compound 1. In particular, the method of the invention is simpler and involves fewer steps than prior art methods and provides Compound 1 in acceptable purity, including acceptable enantiomeric purity.

In one embodiment, the method of the invention comprises steps (a) to (e) as set forth above. In certain embodiments, the method further comprises the step of protecting the amino groups of 1,4-butanediamine,

to produce the compound of Formula I of step (a). The amino groups can be protected using methods and protecting groups known in the art (see Green, T W and Wuts, PGM, *Protective Groups in Organic Synthesis*, New York: John Wiley and Sons, 1999, Chapter 7, incorporated herein by reference). Preferably the protecting group is benzyl or substituted benzyl, such as 4-methoxybenzyl, 3,4-dimethoxybenzyl or 2-hydroxybenzyl. In one embodiment, the 1,4-butanediamine is protected by reaction with benzyl chloride or a substituted benzyl chloride. In another embodiment, the 1,4-butanediamine is protected via reductive amination of benzaldehyde or a substituted benzaldehyde. In particular, the 1,4-butanediamine can be reacted with benzaldehyde or substituted benzaldehyde to form an intermediate imine, which is then reduced to the compound of Formula I wherein PG is benzyl or substituted benzyl. For example, the 1,4-butanediamine can be reacted with the benzaldehyde or substituted benzaldehyde in a suitable solvent and then treated with palladium on carbon in a protic solvent, such as methanol. In a preferred embodiment, the 1,4-butanediamine is protected according to the reaction below.

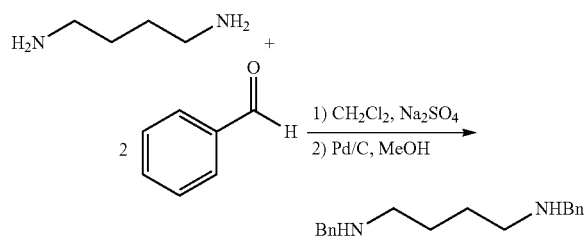

Steps (a) to (e) are discussed in more detail below.

Step (a)

Step (a) involves nucleophilic attack of the protected amino groups of the compound of Formula (I) on the compound of Formula (II). In the compound of Formula (II), X can be any suitable leaving group as is known in the art, such as, but not limited to, chlorine, bromine, iodine, mesylate, benzenesulfonate, tosylate and triflate. Preferably, X is a halogen, such as chlorine or bromine; more preferably, X is chlorine.

The reaction is preferably conducted with at least a stoichiometric amount of the compound of Formula (II), i.e., at least a 2/1 molar ratio of the compound of Formula (II) to the compound of Formula (I). In certain embodiments, an excess of the compound of Formula (II) is used. In certain embodiments, the reaction is conducted with a molar ratio of the compound of Formula (II) to the compound of Formula (I) which is greater than 2/1, for example, from 2/1 to 5/1, and preferably from about 3/1 to about 5/1.

Step (a) is conducted in a polar organic solvent, optionally in the presence of a base. Suitable solvents include, but are not limited to, acetone, N,N-dimethylformamide (DMF), ethanol and combinations thereof. Suitable bases include, but are not limited to, $NaHCO_3$, $K_2CO_3$, and diisopropylethylamine. Preferably, (i) the solvent is ethanol and the base is $NaHCO_3$; (ii) the solvent is DMF, the base is $NaHCO_3$ and the solution optionally further includes NaI; (iii) the solvent is ethanol and the base is diisopropylethylamine; or (iv) the solvent is DMF and the base is $K_2CO_3$. In particularly preferred embodiments, the solvent is ethanol and the base is $NaHCO_3$.

Step (a) can be conducted at any temperature which provides the product in an acceptable period of time, as can be determined by one of skill in the art. In certain embodiments, the reaction is conducted at a temperature at room temperature (25° C.) or greater, for example, from 25° C. to 120° C., 30° C. to 110° C., 40° C. to 100° C., 50° C. to 90° C. or 60° C. to 85° C. In certain embodiments, the reaction is conducted at 75° C. to 90° C. In preferred embodiments, PG is benzyl, X is chloro, the solvent is ethanol, the base is $NaHCO_3$, and the reaction is conducted at a temperature from about 70° C. to about 90° C.

Step (b)

Step (b) involves reduction of the nitrile groups of the compound of Formula (III) to form the primary amino groups of the compound of Formula (IV). Suitable reducing agents are known in the art (see Larock, *Comprehensive Organic Transformations*, VCH: New York, 1989, pp 437-438, incorporated herein by reference). Examples of reducing agents which can be used in this step include, but are not limited to, $LiAlH_4$, $BH_3·Me_2S$, NaOEt, $H_2$/catalyst, $NaBH_4$ in an alcohol solvent in the presence of $CoCl_2$ catalyst, $NaBH_4$/Raney nickel, and methanolic ammonia/Raney nickel. Preferably, the reducing agent is $LiAlH_4$.

Step (b) is conducted in a suitable organic solvent, for example, a polar organic solvent such as, but not limited to, tetrahydrofuran. In one embodiment, the reactants are mixed at a temperature below room temperature, for example, from about −10° C. to about 15° C., preferably from about −5° C. to 10° C., and more preferably from about 0° C. to about 5° C. In this embodiment, the reaction mixture is then preferably warmed to about 20° C. to about 35° C., about 20° C. to about 30° C. or about 25° C. to about 30° C.

Step (c)

Step (c) involves acetylation of the primary amino and hydroxyl groups of the compound of Formula (IV). The acetylating agent can be any suitable acetylating agent as is known in the art. Preferred acetylating agents include acetyl chloride and acetic anhydride.

Step (c) is conducted in a suitable organic solvent, such as a polar organic solvent, and optionally in the presence of a base. Suitable solvents include, but are not limited to, dichloromethane. Suitable bases include, but are not limited to, triethylamine. In one embodiment, the reactants are mixed at a temperature below room temperature, for example, from about −10° C. to about 15° C., preferably from about −5° C. to 10° C., and more preferably from about 0° C. to about 5° C. In this embodiment, the reaction mixture is then preferably warmed to about 20° C. to about 35° C., about 20° C. to about 30° C. or about 25° C. to about 30° C.

Step (d)

Step (d) involves reduction of the acetamido groups and deacetylation of the hydroxyl groups of the compound of Formula (V) to produce the compound of Formula (VI). This reaction is conducted with a suitable reducing agent as is known in the art (see Larock, *Comprehensive Organic Transformations*, VCH: New York, 1989, pp 432-433, incorporated herein by reference). Examples of reducing agents which can be used in this step include $LiAlH_4$, $H_2$/catalyst, $NaBH_4$, borane, sodium in 1-propanol, trichlorosilane and dimethylaminoborohydride. Preferably the reducing agent is $LiAlH_4$.

Step (d) is conducted in a suitable organic solvent, such as a polar organic solvent. Suitable solvents include, but are not limited to, tetrahydrofuran. In one embodiment, the reactants are mixed at a temperature below room temperature, for example, from about −10° C. to about 15° C., preferably from about −5° C. to 10° C., and more preferably from about 0° C. to about 5° C. In this embodiment, the reaction mixture is then preferably initially warmed to about 20° C. to about 35° C., about 20° C. to about 30° C. or about 25° C. to about 30° C. Preferably, the reaction mixture is then further warmed to a temperature of about 40° C. to about 70° C., about 45° C. to about 65° C., about 50° C. to about 60° C. or about 55° C. to about 60° C.

Step (e)

Step (e) is the deprotection of the compound of Formula (VI) to produce Compound 1 or a salt thereof. The deprotection reaction is selected according to the protecting group used as is known in the art (see Green, T W and Wuts, PGM, *Protective Groups in Organic Synthesis*, New York: John Wiley and Sons, 1999, Chapter 7). For example, when the protecting group is benzyl or a substituted benzyl, the compound of Formula (VI) can be deprotected by hydrogenation, for example, using $H_2$ gas and a catalyst, where suitable catalysts include, but are not limited to, palladium on carbon (Pd/C). Step (e) is optionally conducted in the presence of an acid, such as HCl. In this embodiment, the product of step (e) is a salt of Compound 1.

Step (e) is conducted in a suitable organic solvent, such as a polar organic solvent, preferably a protic organic solvent. Suitable solvents include, but are not limited to, $C_1$-$C_4$ alcohols, such as methanol or ethanol. Preferably, the solvent is ethanol.

In certain embodiments, in which the product of step (e) is Compound 1, the method of the invention further includes step (f), the preparation of an acid addition salt of Compound 1. The salt can be produced by reacting Compound 1 with a suitable acid, preferably at about a 4/1 or greater molar ratio of the acid to Compound 1, to produce the desired salt. In a preferred embodiment, Compound 1 is reacted with an about 4/1 molar ratio of HCl to Compound 1 to produce the tetrahydrochloride salt of Compound 1.

In a particularly preferred embodiment of the method of the invention, PG is benzyl, X is chlorine, the reducing agent of steps (b) and (d) is $LiAlH_4$, and the acetylating agent of step (c) is acetic anhydride. In step (e), the compound of Formula (VI) is preferably deprotected with Thin the presence of Pd/C, optionally in the presence of HCl.

It is to be understood that the methods described herein can also be used to produce (6R,15R)-3,8,13,18-tetraazaicosane-6,15-diol by replacing the compound of Formula (II) with its enantiomer, for example, (R)-4-chloro-3-hydroxybutanenitrile. This will result in the compounds of Formulas (III), (IV), (V) and (VI) in which the configuration of each chiral center is inverted, i.e., the enantiomers of the structures illustrated above and the intermediates described in the examples below.

EXEMPLIFICATION (6S,15S)-3,8,13,18-tetraazaicosane-6,15-diol tetrahydrochloride was prepared as described below.

Step 1

Synthesis of $N^1$, $N^4$-dibenzylbutane-1,4-diamine (Compound 2)

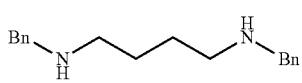

(2)

To a solution of 1,4-diaminobutane (25 g, 0.284 mol, 1 eq) in dichloromethane (250 ml) was added sodium sulfate (120.8 g, 0.851 mol, 3 eq) at 25-30° C. and the resulting mixture was stirred for 10 min at 25-30° C. The reaction mixture was cooled to 10-15° C. and benzaldehyde (63.2 g, 0.596 mol, 2.1 eq) was added at 10-15° C. The reaction mixture was maintained for 2-3 hrs at 10-15° C. Reaction completion was monitored by TLC/HPLC, and when the reaction was deemed complete, the reaction mass was filtered through a celite bed, and the filtrate was concentrated under reduced pressure at 45-50° C. The concentrated filtrate was co-distilled with methanol (50 ml) at 45-50° C. The residue obtained was dissolved in methanol (250 ml) and 10% Pd/C (2.5 g, 10% w/w) was added at 25-30° C. The reaction mixture was kept in a hydrogenation autoclave at 5.0 Kgcm$^{-2}$ pressure at 25-30° C. for 12.0 h at 25-30° C. The reaction progress was monitored by TLC/HPLC. When the reaction was deemed complete, the reaction mixture was filtered through a celite bed, and the filtrate was concentrated under reduced pressure at 45-50° C. The resulting residue was dissolved in ethyl acetate (250 mL) and transferred to a round bottom flask equipped with a nitrogen inlet, an additional funnel, a thermowell and a mechanical stirrer at 25-30° C. Acetic acid (40.5 ml) was added drop wise through an addition funnel to adjust the pH to less than 2.5-3.0. The reaction mass was stirred for 15 min at 25-30° C. and the solid was filtered off, washed with ethyl acetate (50 ml) and dried for 2 h at 25-30° C. The solid was then dissolved in water (250 ml) and basified with sodium hydroxide (10% solution, 300 mL) to adjust the pH to 12 to 12.5 and extracted with ethyl acetate (500 ml*2). The ethyl acetate layer was concentrated under pressure at 45-50° C. and the product (55 g, 72.5% yield) was obtained as a viscous liquid.

$^1$H NMR (400 MHz, MeOH-$d_4$) δ: 1.44(s, 4H), 2.46 (s, 4H), 3.66 (s, 4H), 7.21-7.31 (m, 10H). LCMS (EI) m/e 269 (M+1)

Step 2

Synthesis of (3S,3'S)-4,4'-(butane-1,4-diylbis(benzylazanediyl))bis(3-hydroxybutanenitrile) (Compound 3)

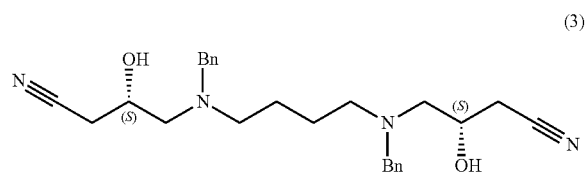

(3)

To a solution of $N^1$, $N^4$-dibenzylbutane-1,4-diamine (90 g, 0.335 mol, 1 eq) in ethanol (900 ml) was added sodium bicarbonate (70.3 g, 0.836 mol, 2.5 eq) and (S)-4-chloro-3-hydroxybutanenitrile (88.2 g, 0.738 mol, 2.2 eq) at 25-30° C. under nitrogen atmosphere. The reaction mixture was heated to 80-85° C. for 24-28 h. The reaction was monitored by TLC/HPLC. As the starting material ($N^1$, $N^4$-dibenzylbutane-1,4-diamine) was not consumed, a second lot of sodium bicarbonate (28.1 g, 0.335 mol, 1.0 eq) and (S)-4-chloro-3-hydroxybutanenitrile (44.1 g, 0.034 mol, 1.1 eq) was added at 80-85° C. and maintained for 16-18 h. The reaction was monitored by TLC/HPLC. As the starting material ($N^1$, $N^4$-dibenzylbutane-1,4-diamine) was not consumed, a third lot of sodium bicarbonate (28.1 g, 0.335 mol, 1.0 eq) and (S)-4-chloro-3-hydroxybutanenitrile (44.1 g, 0.034 mol, 1.1 eq) was added at 80-85° C. and maintained for 16-18 h. The reaction was monitored by TLC/HPLC, and when the reaction was deemed to be complete, the reaction mass was filtered through a celite bed. The filtrate was concentrated under reduced pressure at 45-50° C. followed by addition of the water (1800 ml) at 25-30° C. The reaction mixture was extracted with dichloromethane (1800 ml*2). The organic layer was concentrated and purified with column chromatography using 60-120 silica gel eluting with 40-60% ethyl acetate in petroleum ether. The pure fraction was collected and concentrated under reduced pressure at 45-50° C. and product (65 g, 44.6% yield) was obtained as a viscous liquid.

$^1$H NMR (400 MHz, DMSO-$d_6$) δ:1.35(s, 4H), 2.29-2.34 (m, 4H), 2.36-2.48(m, 6H), 2.64-2.69(m, 4H), 3.53(dd, 4H), 3.82(bs, 2H), 5.23(s, 2H), 7.22-7.33(m, 10H); $^{13}$C NMR (75 MHz, DMSO-$d_6$) δ: 24.0, 24.7, 54.4, 59.3, 59.4, 65.3, 119.5, 127.3, 128.6, 129.1, 139.8; LCMS (EI) m/e 435 (M+1).

Step 3

Synthesis of (2S,2'S)-1,1'-(butane-1,4-diylbis(benzylazanediyl))bis(4-aminobutan-2-ol) (Compound 4)

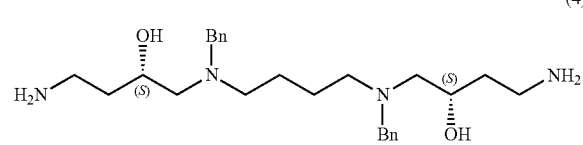

(4)

To a solution of (3S,3'S)-4,4'-(butane-1,4-diylbis(benzylazanediyl))bis(3-hydroxybutanenitrile) (20 g, 0.046 mol, 1 eq) in tetrahydrofuran (400 ml) was added three lots of lithium aluminum hydride (10.5 g, 0.276 mol, 6 eq) at 0-5° C. and the reaction mass was warmed to 25-30° C. The reaction was monitored by TLC/HPLC, and when the reaction was deemed to be complete, the reaction mass was cooled to 0-5° C. and quenched with tetrahydrofuran:water (400 ml). The reaction mass was allowed to warm to 25-30° C. and stirred for 10 min. Sodium sulfate (20 g) was then added and the reaction mass was stirred for 10 min. The reaction mass was filtered through a celite bed and washed with ethyl acetate (200 ml). The organic layer was separated and concentrated under reduced pressure at 45-50° C. The crude material obtained was purified with column chromatography using 230-400 silica gel eluting with (10-20% aqueous ammonia in methanol). The pure fraction was collected and concentrated under reduced pressure at 45-50° C. and the product (10 g, 49.09% yield) was obtained as a viscous liquid.

$^1$H NMR (400 MHz, MeOH-$d_4$) δ: 1.48-1.58(m, 6H), 1.82-1.84(m, 2H), 2.40-2.48(m, 8H), 2.91-2.96(m, 4H), 3.59 (dd, 4H), 3.77-3.79(m, 2H), 7.23-7.32(m, 10H); $^{13}$C NMR (75 MHz, MeOH-$d_4$) δ: 24.4, 33.5, 37.6, 54.0, 58.9, 60.0, 67.0, 126.8, 128.0, 128.9, 139.1; LCMS (EI) m/e 443.3 (M+1).

Step 4

Synthesis of (6S,15S)-8,13-dibenzyl-2,19-dioxo-3,8,13,18-tetraazaicosane-6,15-diyl diacetate (Compound 5)

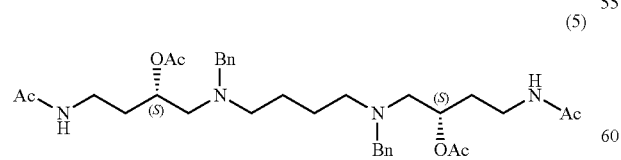

(5)

To a solution of (2S,2'S)-1,1'-(butane-1,4-diylbis(benzylazanediyl))bis(4-aminobutan-2-ol) (11 g, 0.034 mol, 1 eq) in dichloromethane dry (220 ml) was added triethylamine (20.8 ml, 0.149 mol, 6 eq) slowly at 0-5° C. The reaction mass was stirred at the same temperature for 20 min and acetic anhydride (110 ml) was added at 0-5° C. The reaction mass was stirred at 25-30° C. for 18 h. The reaction was monitored by TLC/HPLC, and when deemed to be complete, the reaction mass was concentrated under reduced pressure at 45-50° C. The obtained residue was subjected to column chromatography using 60-120 silica gel eluting with 5% in methanol. The pure fraction was collected and concentrated under reduced pressure at 45-50° C., and the product (8 g; 52.7% yield) was obtained as a viscous liquid.

$^1$H NMR (400 MHz, MeOH-$d_4$) δ: 1.43(s, 4H), 1.59-1.65 (m, 2H), 1.83-1.89(m, 2H), 1.92(s, 6H), 2.04(s, 6H), 2.32-2.45(m, 6H), 2.56-2.62(m, 2H), 3.16(t, 4H), 3.56(dd, 4H), 5.02-5.06(m, 2H), 7.20-7.30(m, 10H); LCMS (0) m/e 611.2 (M+1).

Step 5

Synthesis of (6S,15S)-8,13-dibenzyl-3,8,13,18-tetraazaicosane-6,15-diol (Compound 6)

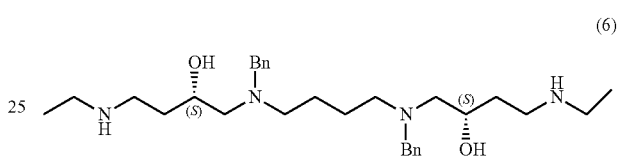

(6)

To a solution of ((6S,15S)-8,13-dibenzyl-2,19-dioxo-3,8, 13,18-tetraazaicosane-6,15-diyl diacetate) (6 g, 0.009 mol, 1 eq) in THF (40 ml) was added lithium aluminum hydride lot wise (3.7 g, 0.098 mol, 10 eq) at 0-5° C. The reaction mass was allowed to warm to 25-30° C. and then maintained at 55-60° C. for 3h. The reaction was monitored by TLC/ HPLC, and when deemed to be complete, the reaction mass was quenched with a water:tetrahydrofuran mixture (30 ml). Sodium sulfate (20 g) was added to the reaction mass and stirred for 10 min. The reaction mass was filtered through a celite bed and washed with ethyl acetate (200 ml) and saturated sodium chloride solution (48 ml) and the organic layer was concentrated at 45-50° C. The crude material obtained was subjected to purification by acid and base extraction process. The crude material was dissolved in dichloromethane (60 ml) and 1.5N hydrochloric acid (24 ml) was added. The mixture was stirred for 15 min at 25-30° C. and the aqueous layer was separated. The aqueous layer was basified with 10% sodium bicarbonate to a pH of 8-9. The aqueous layer was washed with methyl tertiary butyl ether (36 ml*2). The aqueous layer was then washed with ethyl acetate (36 ml*2) and finally extracted with dichloromethane (60 ml*2). The combined organic layer was then washed with water (30 ml). The organic layer was concentrated under reduced pressure at 45-50° C. and the product (3 g, 61.0% yield) was obtained as a viscous liquid. $^1$H NMR (400 MHz, MeOH-$d_4$) δ: 1.12(t, 6H), 1.49(s, 6H),1.72-1.76(m, 6H), 1.72-1.76(m, 2H), 2.42-2.43(m, 8H), 2.60-2.72(m, 8H), 3.60(m, 2H), 3.713-3.727(m, 2H), 7.241-7.324(m, 10H); LCMS (EI) m/e 499.4 (M+1).

Step 6

Synthesis of (6S,15S)-3,8,13,18-tetraazaicosane-6,15-diol tetrahydrochloride

To a solution of HCl in 1,4-dioxane (4 M, 35 ml) was added [(6S,15S)-8,13-dibenzyl-3,8,13,18-tetraazaicosane-6, 15-diol] (3.5 g, 0.007 mol, 1.0 eq) at 25-30° C. and the resulting mixture was stirred at 25-30° C. for 1 h. The reaction mixture was concentrated under reduced pressure at 50-55° C. The solid obtained was dissolved in ethanol (80 ml) and water (42 ml). The solution was transferred to a hydrogenator and Pd/C (50% wet, 3.5 g) was added. The reaction mixture was maintained at 5 Kgcm$^{-2}$ hydrogen pressure at 25-30° C. for 18 h. The reaction was monitored by $^1$H NMR/HPLC. When the reaction was deemed to be complete, the reaction mass was filtered through a celite bed and washed with water:ethanol (1:1, 35 ml) and then concentrated HCl (7 ml) was added. The mixture was stirred at 25-30° C. for 30 min, then concentrated under reduced pressure at 45-50° C. and stripped off with ethanol (35 ml). The residue obtained was stirred with 20% methanol in dichloromethane solution at 25-30° C. for 1 h. The solid obtained was filtered and treated with 5% aqueous ethanol (35 ml) under reflux at 75-80° C. for 1 h. The reaction mass was cooled to 25-30° C. and further cooled to 0-5° C. and maintained at 0-5° C. for 2 h, filtered, and the solid obtained was subjected to aqueous ethanol purification. The white solid was further dried at 50-55° C. for 5 h to provide the product (700 mg, 31.3% yield).

$^1$H NMR (400 MHz, D$_2$O) δ: 1.15 (t, 6H), 1.80-1.85(m, 8H), 2.91-3.14(m, 16H), 3.92-3.96(m, 2H); $^{13}$C NMR (75 MHz, MeOH-d$_4$) δ: 10.5, 22.6, 30.4, 43.0, 43.8, 47.0, 52.1, 64.6; LCMS (EI) m/e 319.2 (M++1 (free base)).

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:
1. A method of producing Compound 1 or a salt thereof,

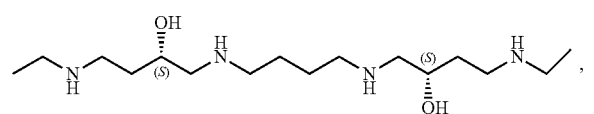

comprising the steps of:
(a) reacting a compound of Formula (I),

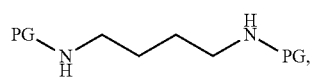

wherein each PG is an amino protecting group,
with a compound of Formula (II),

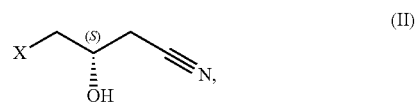

wherein X is a leaving group;
thereby producing a compound of Formula (III),

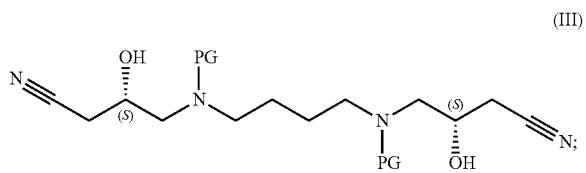

(b) reacting the compound of Formula (III) with a reducing agent, thereby producing a compound of Formula (IV),

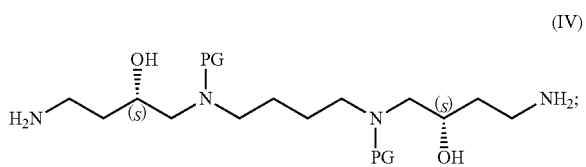

(c) reacting the compound of Formula (IV) with an acetylating agent thereby producing a compound of Formula (V),

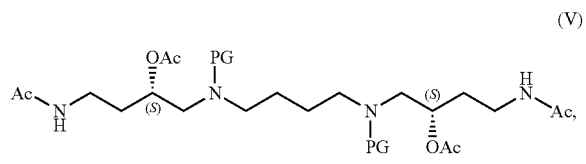

(d) reacting the compound of Formula (V) with a reducing agent, thereby producing a compound of Formula (VI),

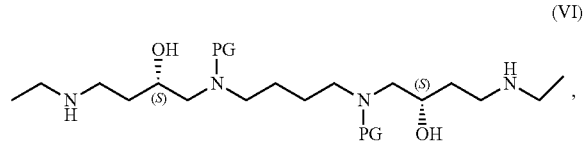

and
(e) deprotecting the compound of Formula (VI), optionally in the presence of an acid, thereby producing Compound 1 or a salt thereof.

2. The method of claim 1, wherein PG is benzyl or substituted benzyl.

3. The method of claim 2, wherein PG is benzyl, 4-methoxybenzyl or 3,4-dimethoxybenzyl.

4. The method of claim 3, wherein PG is benzyl.

5. The method of claim 2, wherein in step (e), the compound of Formula (VI) is deprotected by hydrogenolysis.

6. The method of claim 4, further comprising the step of reacting 1,4-diaminobutane with benzaldehyde under reducing conditions, thereby producing the compound of Formula (I).

7. The method of claim 1, wherein the reducing agent of step (b) is lithium aluminum hydride.

8. The method of claim 1, wherein the acetylating agent is acetic anhydride.

9. The method of claim 1, wherein the reducing agent of step (d) is lithium aluminum hydride.

10. The method of claim 1, wherein PG is benzyl; the reducing agent of step (b) and the reducing agent of step (d) are both lithium aluminum hydride; and the acetylating agent is acetic anhydride.

11. The method of claim 1, wherein step (a) is conducted in the presence of a base.

12. The method of claim 11, wherein the base is $K_2CO_3$, $NaHCO_3$ or diisopropylethylamine.

13. The method of claim 11, where step (a) is conducted in a polar organic solvent.

14. The method of claim 13, wherein the solvent is ethanol, N,N-dimethylformamide, or acetone.

15. The method of claim 1, wherein step (a) is conducted in an ethanol solution of sodium bicarbonate.

16. The method of claim 1, wherein the reducing agent in step (b) is lithium aluminum hydride or Raney nickel and ammonia.

17. The method of claim 1, wherein step (b) is conducted in tetrahydrofuran or methanolic ammonia.

* * * * *